(12) United States Patent
Panero et al.

(10) Patent No.: US 7,253,152 B2
(45) Date of Patent: Aug. 7, 2007

(54) ELECTRICALLY CONDUCTIVE POLYMERIC BIOMATERIALS, THE PROCESS FOR THEIR PREPARATION AND THE USE THEREOF IN THE BIOMEDICAL AND HEALTHCARE FIELD

(75) Inventors: Stefania Panero, Rome (IT); Gianluca Abbati, Rome (IT); Davide Renier, Mestrino (IT); Vittorio Crescenzi, Rome (IT)

(73) Assignee: Fidia Advanced Biopolymers s.r.l., Abano Terme (IT)

( * ) Notice: Subject to any disclaimer, the term of this patent is extended or adjusted under 35 U.S.C. 154(b) by 553 days.

(21) Appl. No.: 10/476,854

(22) PCT Filed: Apr. 29, 2002

(86) PCT No.: PCT/EP02/04708

§ 371 (c)(1),
(2), (4) Date: Feb. 6, 2004

(87) PCT Pub. No.: WO03/000309

PCT Pub. Date: Jan. 3, 2003

(65) Prior Publication Data

US 2004/0131651 A1     Jul. 8, 2004

(30) Foreign Application Priority Data

May 8, 2001 (IT) .......................... PD2001A0108

(51) Int. Cl.
*A01N 43/04* (2006.01)
*A61K 31/715* (2006.01)
*C07H 1/00* (2006.01)

(52) U.S. Cl. ................. 514/54; 536/123.1; 536/123.12

(58) Field of Classification Search ............. 536/123.1, 536/123.12; 514/54
See application file for complete search history.

(56) References Cited

FOREIGN PATENT DOCUMENTS

| WO | WO 89/03876 A1 | 5/1989 |
| WO | WO 95/25751 A1 | 9/1995 |
| WO | WO 96/04340 A1 | 2/1996 |
| WO | WO 97/16545 A1 | 5/1997 |

OTHER PUBLICATIONS

Collier et al. Journal of Biomedical Materials Research (Jun. 2000), vol. 50, pp. 574-584.*
Collier J H et al.: Journal of Biomedical Materials Research, vol. 50, No. 4, (Jun. 15, 2000), pp. 574-585, XP009001195.
Garner B et al.: Journal of Biomedical Materials Research, vol. 44, (Feb. 1999), pp. 121-129, XP000964695.

* cited by examiner

*Primary Examiner*—Patrick Lewis
(74) *Attorney, Agent, or Firm*—Birch, Stewart, Kolasch & Birch, LLP

(57) ABSTRACT

The present invention concerns the preparation of composite biomaterials constituted by hyaluronic acid and the derivatives thereof in combination with polymers that have electrically conductive properties. In particular, the methods of preparing biomedical devices formed by a two- or three-dimensional polysaccharide matrix and by an electrically conductive membrane. The matrix is constituted by hyaluronic acid derivatives in the form of membranes, woven fabrics, nonwoven felts, meshes, gauzes, guide channels or sponges, while the electrically conductive membrane is constituted by a film of polypyrrole (polymer conductor) in combination with hyaluronic acid or a derivative thereof (doping agent).

20 Claims, 3 Drawing Sheets

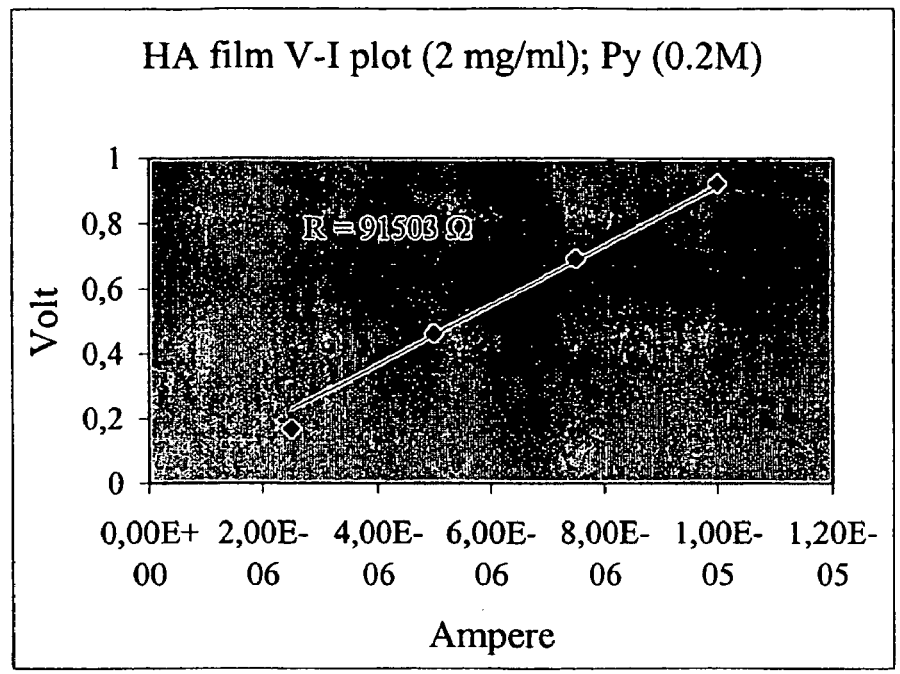
Fig. 1A: V-I plot for conductive polymer films based on HA and Py.
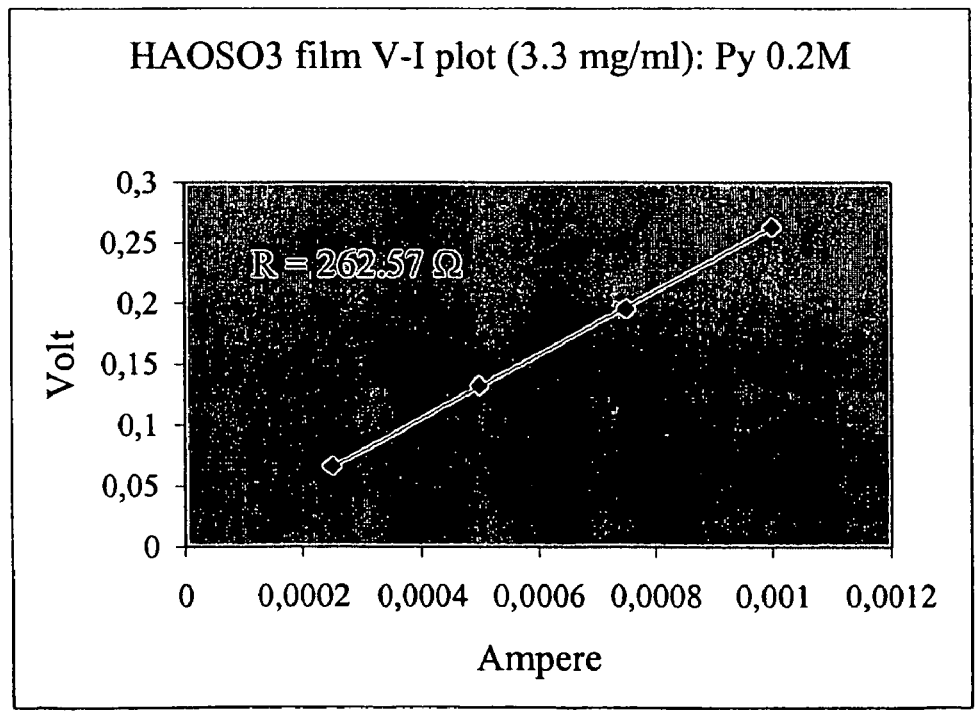
Fig. 1B: V-I plot for conductive polymer films based on HAOSO$_3$ and Py.

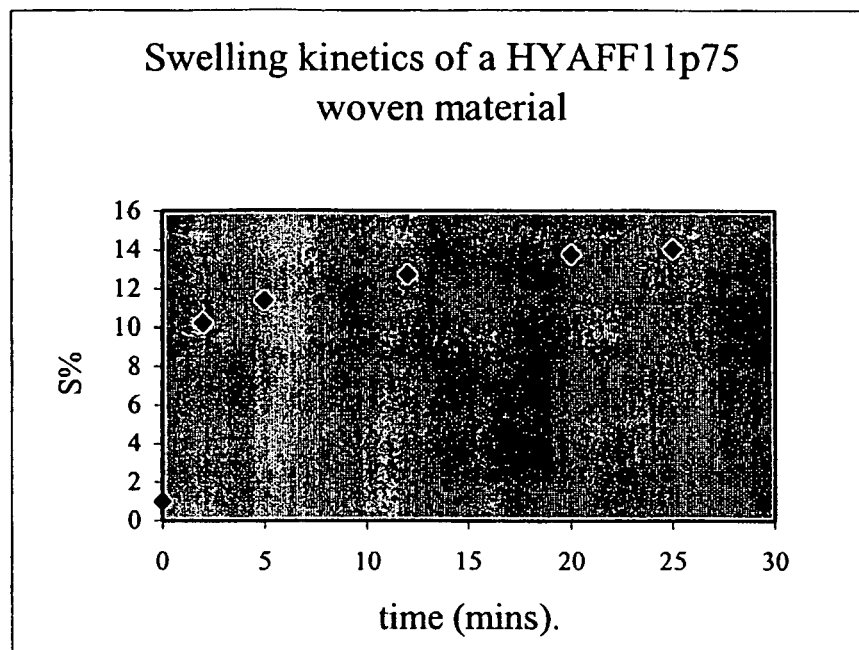
Fig. 2: swelling kinetics of a HYAFF®11p75 woven material in an aqueous solution in the presence of $HAOSO_3$ 3.3 mg/ml and Py 0.1M.

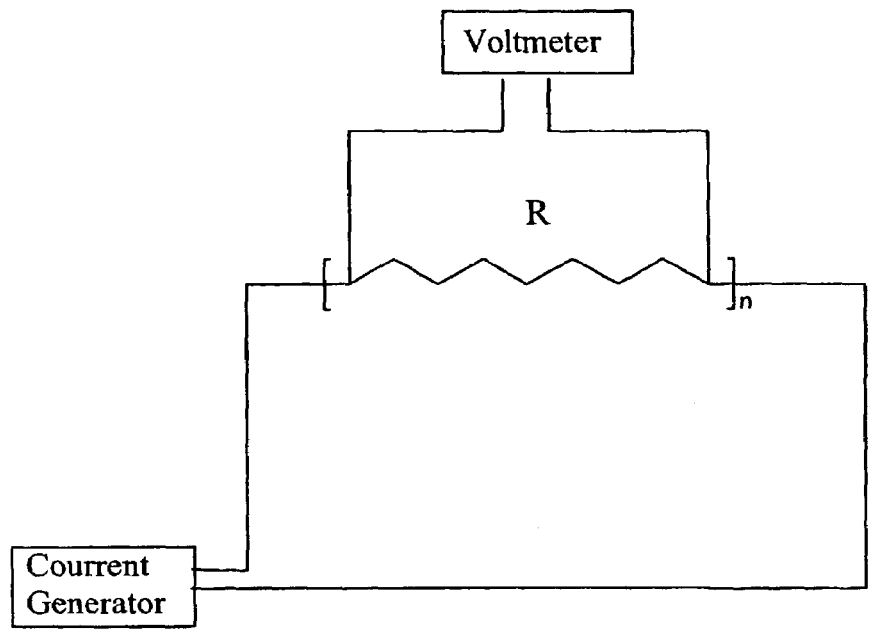
Figure 3: Scheme of a generic circuit with serial electrochemical cells
Where:
R = electrochemical cell
n = indicates the number, variable, of cells that can be connected in a series.

ELECTRICALLY CONDUCTIVE POLYMERIC BIOMATERIALS, THE PROCESS FOR THEIR PREPARATION AND THE USE THEREOF IN THE BIOMEDICAL AND HEALTHCARE FIELD

This application is the national phase under 35 U.S.C. § 371 of PCT International Application No. PCT/EP02/04708 which has an International filing date of April 29, 2002, which designated the United States of America.

SUBJECT OF THE INVENTION

The present invention concerns the preparation of composite biomaterials constituted by hyaluronic acid and the derivatives thereof in combination with polymers that have electrically conductive properties.

In particular, the methods of preparing biomedical devices formed by a two- or three-dimensional polysaccharide matrix and by an electrically conductive membrane. The matrix is constituted by hyaluronic acid derivatives in the form of membranes, woven fabrics, nonwoven felts, meshes, gauzes, guide channels or sponges, while the electrically conductive membrane is constituted by a film of polypyrrole (polymer conductor) in combination with hyaluronic acid or a derivative thereof (doping agent).

The synergic biological and physical action of the natural polysaccharide component, with a capacity for accelerating the processes of tissue regeneration, and the peculiar characteristic of the synthetic polymer of conducting electric charges, makes it possible to use such biomaterials to advantage in the field of nerve and bone regeneration.

BACKGROUND OF THE INVENTION

Hyaluronic acid is a natural, linear polysaccharide constituted by a repetitive monomeric unit formed by d-glucuronic acid and N-acetylglucosamine. It is to be found in almost all the soft tissues of higher organisms and plays a vital role in many biological processes linked with the repair and recovery of tissue function.

Hyaluronic acid derivatives and their transformation into biomaterials such as, for example, membranes, nonwoven felts, meshes and sponges, for use in the biomedical and surgical fields, have been amply described in patent No. EP 0216453 B1. The key property of these products is their biodegradability, because once they have been implanted in the application site, they favour the release of native hyaluronic acid that is able to exercise its own biological functions (D. Campoccia et al., Biomaterials, vol. 19 (1998), page 2101).

Among other applications for ester derivatives of hyaluronic acid, EP 0652778 B1 claims the preparation of guide channels constituted by a combination of meshes immersed in a continuous polysaccharide matrix. Although these devices seem in some way to favour the growth of neurites and axons in short sections of damaged nerves, they are not able fully to support the process of repairing nerve function because of their rapid degradation.

It is an accepted fact that electric charges carried by a conductive material play a decisive role in increasing neuronal length and thereby accelerating nerve regeneration. In order to obtain these results, past techniques have exploited electric and magnetic fields generated externally or by introducing electric current directly through a section of damaged nerve. Neuronal growth has been demonstrated using materials with piezoelectric properties, such as polyvinylene difluoride (PVDF), the effect of which is attributable to the transient surface charges generated as a result of repeated mechanical stress. (R. F. Valentini et al., biomaterials, vol. 13, page 183 (1992)). The application of exogenous electromagnetic fields in in vitro and in vivo studies has shown better migration of the neuronal cells, this effect probably being due to a combination of biological mechanisms that depend on the redistribution of cytoskeletal proteins, such as actin and other molecules, on modifications in their formation and their capacity for favouring electric signals between parts of damaged nerve.

Although all these systems have proved to be partially effective, the use of piezoelectric materials and external electromagnetic fields have strong limitations. Without outside stimulation, the former are only able to generate electric properties for a limited period only, often insufficient for the functions they are to perform. Electromagnetic fields, on the other hand, cannot be focused exclusively on the nerve area to be regenerated and this may have unwanted effects on the surrounding healthy tissues.

More recently, polypyrrole has been used as a polymer to conduct electric signals in the biomedical field. Some particular applications described in the literature suggest that polypyrrole is a suitable matrix for the release of neurotransmitters or to make biosensors in association with other polymers and as a biomaterial with electroconductive properties to be used in the sector of nerve regeneration (V. Shastri et al., WO 97/16545; C. Schmidt, Tissue Engineering, vol. 26, 1999, page 617; J. Collier et al., Biomed. Mater. Res., 50, 2000, page 574). The special biological function demonstrated by polypyrrole (enabling nerve cells to take and grow) seems to be closely linked with the state of oxidation and the degree of hydrophilia due to the association with a particular doping agent, that may be constituted by an inorganic salt or by an anionic polysaccharide or polymer.

G. Robila et al. (J. Of Applied Polymer Sci., vol. 66, 1997, page 591) describe the use of polyurethane sulphate as a doping agent for use in making composite biomaterials based on polypyrrole, while C. Schmidt et al. (Proc. Nat. Acad. Sci. USA, vol. 94, 1997, page 8948) present a series of results from in vitro and in vivo studies to determine the cell response induced by the implantation of a composite biomaterial constituted by polypyrrole in association with polystyrene sulphate as doping agent.

Among the hyaluronic acid derivatives with a marked anionic charge linked with the type of chemical modification conducted on the polymer chain, of particular interest are those obtained by substituting the hydroxy functions with sulphated groups. These composites have already been described by Barbucci et al (EP 0702699 B1), who detail the preparation of biopolymers with anticoagulant properties intended for biomedical applications where there is contact with the blood. Again for the preparation of biomaterials with haemocompatible properties, the same R. Barbucci describes, in patent application No. PCT WO99/43728, composites constituted by polyurethane chemically linked with sulphated hyaluronic acid derivatives.

Although the electropolymerisation reaction of pyrrole with HA and polystyrene sulphonate (PSS) is well known as a procedure of synthesis to obtain biocompatible polymer films, both in the form of a single layer (PPy/HA and PPy/PSS) and as multiple layers ("Synthesis and characterisation of polypyrrole-hyaluronic acid composite biomaterials for tissue engineering applications", Collier et al., J. Biomed. Mater. Res., 50, 574-584, 2000; PCT Publication No. WO 97/16545), the inventive aspect that characterises the present invention consists in using esterified hyaluronic acid derivatives (HYAFF®), e.g. in the form of woven, non-woven fabrics and guide channels, as supporting materials on which to activate the polymerisation reaction between PPy and PSS, hyaluronic acid, HAOSO$_3$, HYOXX™ and the derivatives thereof, obtaining composites that can be grafted directly into living organisms.

DETAILED DESCRIPTION OF THE INVENTION

The present invention describes the preparation of polymer films that are electric conductors based on polypyrrole (PPy), hyaluronic acid (HA) and its sulphated derivatives (HAOSO$_3$) and hypercarboxylates (HTOXX™), either supported or not supported on woven, non-woven fabrics and membranes constituted by benzyl esters of hyaluronic acid (woven and non-woven fabrics based on HYAFF®11p75 and total HYAFF®11 with a higher degree of esterification), to obtain materials for use in the biomedical sector for the regeneration of nerve and bone tissue (for example for the growth and differentiation of nerve cells, the regeneration of bone tissue using supporting materials, the repair of damaged nerves and consequent recovery of lost nervous function).

A) Electrically Conductive Polymers

Polypyrrole belongs to the class of polymer materials that are able to vary electric conductibility following a suitable redox reaction, commonly known as doping. It involves the transformation of the neutral-isolating polymer into an ionic complex formed by a polymer cation and a counterion (which is the reduced form of the oxidating agent, doping p) or by a polymer anion and a counterion (which is the oxidised form of the reducing agent, doping n) as indicated in Scheme 1:

POLYMER+Electron Attractor (POLYMER)$^+$+(EA)$^-$: p type doping

POLYMER+Electron Donor (POLYMER)$^-$+(ED)$^+$: n type doping

Scheme 1: Typical p and n Type Doping for Semiconductor Polymers

The processes of conduction are performed by electrons belonging to π-conjugated molecular systems and, therefore, having a high delocalised charge density. In these materials, the doping mechanism, unlike in the case of semiconductors of an organic nature, generally occurs by a redox reaction between the polymer and the doping agent used. Once doped, the polymer undergoes both structural and electronic modification, with consequent redistribution of the electrons belonging to the π-conjugated system into a new series of energy levels, interposed between the valence and conduction bands. The number of these energy levels and their electronic population depend on the structure of the polymer, on the concentration and on the type of doping agent used and the possible presence of degenerate isomeric states (e.g. soliton system of polyacetylene, polar and/or bipolar systems). Among the more representative conductive polymers, we find polyacetylene, polypyrrole, polythiophene, polyaniline, polyphenylene sulphide, poly-p-phenylene, polyphenylene-vinylene and the derivatives thereof. These present a very high application potential that ranges from the field of electrochromic visualisers to materials for biomedical use, exploiting both their different values of electric conductibility, according to the counterions used as dopers, and their different chemical stability in air.

The high degree of conjugation presented by the polymer chains favours processes of charge transfer to inter- and intrachain, giving rise to a conduction phenomenon known as hopping. Generally, the conductor polycation (if the effect of the doping agent is type p) is associated with an anion that guarantees its total electroneutrality and that is indicated in the following scheme as X' (where X' may represent PSS, HA, HAOSO$_3$, HYOXX™ and the derivatives thereof, heparin, polyethylene sulphonate, dextran.sulphate, biologically active molecules, sulphonated and sulphated biological molecules and macromolecules):

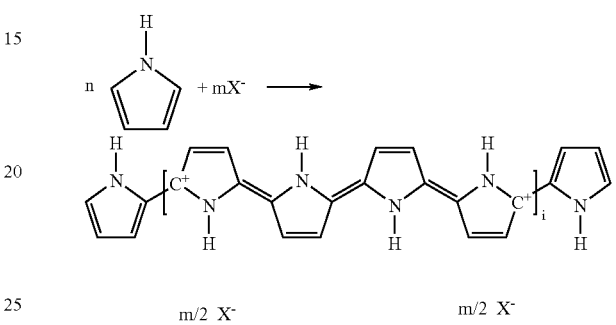

where:

$i = (n - 2)$

X=doping agent.

Scheme 2: Bipolar Structure of Polypyrrole

B) Mechanism of the Synthesis of Polypyrrole

The synthesis of polypyrrole can be conducted both chemically and electrochemically, polarising the monomer in a suitable cell. It is interesting to note that the polymerisation and oxidation of the polymer can be achieved in a single anodic operation. Indeed, the process of polymerisation of pyrrole, in its oxidised form, occurs by the formation of a series of radical-cationic intermediates with different molecular weights. As shown in Scheme 3 ("Electrically conductive polymers", Mark Bikales, Encyclopaedia of polymer science and engineering, vol. 5, page 594), the polymerisation reaction begins with the formation of a monomeric radical-cation (initiation process) type HPH$^{.+}$; this intermediate generates, by means of a coupling process, a dimer with a double positive charge (HPPH$^{2+}$), that is subsequently converted into its radical-cationic form (HPPH$^{.+}$). The reaction then proceeds with the formation of a series of "radical-cationic" intermediates with increasing molecular weights (propagation) until a polymer is obtained in its oxidised form associated with an anion every 3-4 monomeric units (termination).

Initiation

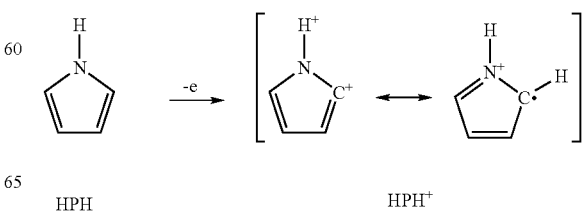

HPH                         HPH$^+$

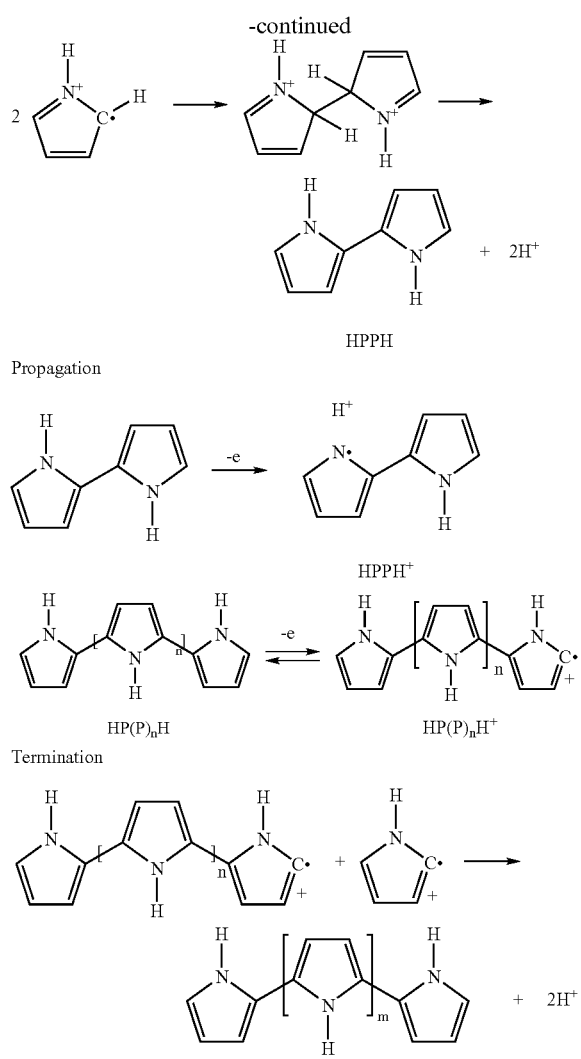

Scheme 3: Electropolymerisation of Pyrrole (Py). Stoichiometry of the entire synthesis process therefore involves three consecutive reaction steps, two of which are of an irreversible nature and one a state of equilibrium between the neutral polymer form, or reduced $(HP(P)_nPH)$, and its oxidised form $(HP(P)_nPH^{(nx)+})$.

The polymer, having a lower redox potential than the monomer is subject to further oxidative phenomena that lead to the formation of electrically charged sites distributed in a chain as described in point 3 of Scheme 4.

1. $(n+2)HPH \rightarrow HP(P)_nPH^{(nx)+}+(2n+2)H^++(2n+2+nx)e^-$

2. $(n+2)HPH \rightarrow HP(P)_nPH+(2n+2)H^++(2n+2)e^-$

3. $HP(P)_nPH \rightarrow HP(P)_nPH^{(nx)+}+(nx)e^-$

Scheme 4: Scheme of the Synthesis of Polypyrrole Divided into Three Subsequent Reaction Steps; the Aromatic Ring of Py is Indicated with HPH.

C) Conduction Mechanism in a Conductive Polymer

During the redox process, there is an evolution of the electronic structure of the polymer, which explains the conduction mechanism of a polymer material.

The evolution of the structure in bands, that leads to the creation of bipolar states with a high level of doping, justifies how the bipolarones are able to move and thus conduct currents when an electric field is applied. The current is not transported by electrons, as in the case of inorganic semiconductors, but by mobile bipolarones. This mechanism requires the transport of negative counterions that have to spread along the polymer chain to balance the movement of the positive charges, and this means that the conduction mechanism in a polymer requires both electronic and ionic movement. The fact that electric transport also implies ionic transport is vital in practical application. Indeed, ionic transport is far slower than electronic transport, so the kinetics of the process is controlled by the diffusion of the counterions in the polymer matrix.

D) Description of Electrochemical Synthesis

Pyrrole can be purified either by filtration in a column containing activated alumina, keeping the entire system in the dark and at a temperature of between 0 and 4°C. (a procedure that side-steps any degrading effects of the polymer), or by distillation under vacuum (b.p. 131° C). This polymerisation process involves the use of aqueous electrolytic solutions based on polystyrene sulphonate (PSS), hyaluronic acid (HA) ("Synthesis and characterisation of polypyrrole-hyaluronic acid composite biomaterials for tissue engineering applications", Collier et al., J. Biomed. Mater. Res., 50, 574-584, 2000) and the derivatives thereof (sulphated and superoxidated) at different concentrations (within a range of 1 mg/ml to 5 mg/ml) and with different molecular weights (30-2000 Kda). Redistilled water, that is necessary for the preparation of electrolytic solutions, is used for these synthesis procedures, in order to prevent any anions that might alter the yield of the reactive process becoming inserted in the growing polymer (for example, the insertion of $Cl^-$ ions instead of the desired polysaccharide counterion). Once the water has been redistilled it is treated with $KMnO_4$ in order to oxidise any organic residue that may be present. Before starting the synthesis procedure, the electrolytic solution containing pyrrole is "degassed" with a flow of Ar (or nitrogen with >99.99% purity) for about 20 minutes.

These polymerisation procedures were performed using both the galvanostatic and potentiostatic methods. The former, however, gave better results in terms of superficial homogeneity of the films that were obtained, markedly reducing the reaction times. The galvanostatic method enables the synthesis procedures to be performed by applying a current in the electrochemical cell at a constant rate. In this way, since the intensity of the circulating current is known (ranging between 0.5 and 10 mA) as is the surface of the anode immersed in the electrolytic solution (1.5-3 cm²), it was possible to trace both the current in the cell, expressed in mC in relation to time, and the thicknesses of the polymer films obtained ("Handbook of conducting polymers", Diaz & Burgon, vol 1, 81; Ed. Terje A. Skotheim).

An electrochemical cell with two electrodes was used for this type of polymerisation. The working electrode was constituted by a glass covered with a conductive layer in ITO (indium-tin-oxide), e.g. 50'Ω sheets, and a counter-electrode mainly in stainless steel (SS304) or copper. The synthesis procedures were performed using volumes of electrolytic solutions varying between 10 and 25 ml and keeping an average distance between the electrodes of about 1.5 cm.

EXAMPLE 1

Synthesis of Thin Films of PPy/PSS

The synthesis of thin films based on polypyrrole doped with polystyrene sulphonate was performed by both the potentiostatic and galvanostatic methods. For both these synthesis procedures the relative thickness adjusted to the surfaces of the electrodes used and for the current in the cell are reported in Table 1. For these films the thickness were determined indirectly by a procedure devised by Diaz and co-workers ("Handbook of conducting polymers", Diaz & Burgon, vol 1, 81; Ed. Terje A. Skotheim).

The starting electrolytic solutions were prepared using concentrations of anion, lyophilised and in the form of sodium salt, varying between 0.05.0.2M and concentrations of pyrrole between 0.05 and 0.3M. In this way the optimal conditions were established for obtaining films that were homogeneous and easily separable from the working electrode, in order to be able to characterise them from a chemical-physical point of view. This procedure was repeated for the synthesis of new samples based on PPy, HA and the derivatives thereof (sulphated and superoxidised).

The following table reports the synthesis methods used and also the thickness of the films obtained keeping the concentrations of reagent in the solution constant and varying both the current in the cell and the wet surface of the electrodes.

TABLE 1

| Type of film | Method | Thickness (μm) |
| --- | --- | --- |
| PSS 0.1 M; Py 0.1 M | Potentiostatic V = 720 mV vs SCE, 1.2 C | 5.1 |
| PSS 0.1 M; Py 0.1 M | Potentiostatic V = 720 mV vs SCE, 1.8 C | 15.0 |
| PSS 0.1 M; Py 0.1 M | Galvanostatic Total charge → 10.98 C | 46.0 |
| PSS 0.1 M; Py 0.1 M | Galvanostatic Total charge → 7.5 C | 18.4 |

On these films it was also possible to measure electric conductibility, by the technique of the four dots in a line ("Electrically conductive polymers"; Mark Bikales, Encyclopaedia of Polymer Science and Engineering, vol. 5, page 473; "Standard test methods for resistivity of semiconductor materials", ASTM F Regulations 43-93; "Low level measurements", Keithley, $4^{th}$ Ed.).

EXAMPLE 2

Synthesis of Thin Films of PPy/HA

Conductive polymer films based on PPy and HA were synthesised both by a galvanostatic method, applying current at a constant intensity ranging between 0.5 and 10 mA and for periods varying between 60 and 150 minutes, and by the potentiostatic method, using constant potentials ranging between 0.3-0.75 V vs. SCE. The first method was chosen to conduct most of the syntheses, because it enabled us to obtain films with even surfaces, notably reducing the reaction times. The polymer films were synthesised in aqueous solutions using concentrations of Py varying between 0.05 and 0.3 M and concentrations of HA (lyophilised and in the form of a sodium salt: $HA^-/Na^+$) ranging between 0.9 and 5 mg/ml. Table 2 below reports the methods and the experimental conditions:

TABLE 2

| Type of film | Method | Thickness (μm) |
| --- | --- | --- |
| HA 2 mg/ml, Py 0.1M | Potentiostatic V = 720 mV vs SCE, 0.19 C | 0.33 |
| HA 2 mg/ml, Py 0.1M | Galvanostatic Total charge → 1 C | 4.2 |
| HA 2 mg/ml, Py 0.1M | Galvanostatic Total charge → 5 C | 8.4 |
| HA 2 mg/ml, Py 0.1M | Galvanostatic Total charge → 6.24 C | 18 |
| HA 4 mg/ml, Py 0.2M | Galvanostatic Total charge → 6 C | 12 |

In this case too, the thicknesses reported in the table, expressed in μm, were adjusted for the wet surface of the anode and for the current in the cell.

EXAMPLE 3

Synthesis of Thin Films of PPy/HAOSO$_3$

During synthesis, a sulphated derivative of HA, lyophilised and in the form of a sodium salt ($HAOSO_3/Na$) was used as doping agent for polypyrrole, in order to increase the interaction between the positive charges constituting the bipolar system of polypyrrole and the negative charges present along the polysaccharide chain. This new compound gave far better results in terms of electric conduction (see example 4) than the films of PPy/HA. For this type of synthesis we used electrolytic solutions with different molar concentrations of polysaccharide (0.95-5 mg/ml), calculated with regard to the mean degree of sulphation of the repetitive unit of HA.

Unlike the films obtained using HA as such, those based on sulphated HA are more homogeneous and simpler to synthesise. The results reported in Table 3 refer exclusively to films of $PPy/HAOSO_3^-$ in which the polysaccharide is present both at the same molar concentration (moles calculated according to the carboxy function) as that proposed in the literature for HA (2 mg/ml$\equiv 5*10^{-6}$ mole/ml) and at a concentration 3.5 times smaller than that used for the starting polysaccharide (we indicated this mew molar ratio as 1:3:5, corresponding to 0.9 mg/ml). This means that according to the degree of sulphation used (in this case ~2.5-3 sulphate groups per repetitive unit) we worked with a quantity of charge, distributed along the polymer chain of the $HAOSO_3$, that was comparable with that present in the HA as such (2 mg/ml). Another synthetic approach then led us to vary the concentration of pyrrole (from 0.05 to 0.3M) keeping that of $HAOSO_3^-$ constant: the outcome of the synthesis was good, as in over 60 minutes, we obtained films with a thickness of more than 7 μm, whose electric conduction it was possible to measure by means of the four dots in a line technique.

TABLE 3

| Type of film | method | Thickness (μm) |
| --- | --- | --- |
| HAOSO$_3$ 3.3 mg/ml, Py0.1M | Galvanostatic Total charge → 1 C | 1.40 |
| HAOSO$_3$ 3.3 mg/ml, Py0.1M | Galvanostatic Total charge → 4 C | 5.50 |
| HAOSO$_3$ 3.3 mg/ml, Py0.1M | Galvanostatic Total charge → 3 C | 4.20 |
| HAOSO$_3$ 3.3 mg/ml, Py0.2M | Galvanostatic Total charge → 11.88 C | 23.80 |

TABLE 3-continued

| Type of film | method | Thickness (μm) |
|---|---|---|
| HAOSO$_3$ 3.3 mg/ml, Py0.2M | Galvanostatic Total charge → 8.8 C | 7.10 |
| HAOSO$_3$ 3.3 mg/ml, Py0.2M | Galvanostatic Total charge → 10.8 C | 13.75 |
| HAOSO$_3$ 3.3 mg/ml, Py0.2M | Galvanostatic Total charge → 5.82 C | 12.40 |

EXAMPLE 4

Electric Conduction Measurements

It was possible to perform electrical characterisation on the polypyrrole-based polymers. This allowed us to determine, for each synthesised species, the corresponding value of intrinsic conductibility (σ), estimated by inverting the specific resistivity (ρ) of the material, and expressed as:

$$\rho = \frac{\pi}{\ln 2} * \frac{V}{I} * d$$

where d (cm) indicates the thickness of the sample, while the ratio between the potential (V) and the current (I) indicates the resistance (R in Ω). This equation, valid for the four dots in a line technique, is applicable only when the distance between the electrodes is at least one order of magnitude greater than the thickness of the sample used and when the test material is deposited on a non-conductive substrate. By representing as a graph the pattern of the difference of potential measured, in relation to the intensity of the current applied, a straight line is obtained, the slope of which gives the resistance of the material (FIG. 1) and, therefore, its conductibility.

Table 4 reports the values of electric conductibility calculated for the samples synthesised using different experimental conditions (in terms of concentration of Py and counterion in solution).

TABLE 4

| Polypyrrole/counterion coupling | Conductibility [S/cm] |
|---|---|
| PSS 0.1M; Py 0.1M | (0.067 ± 0.003) |
| PSS 0.1M; Py 0.2M | (0.80 ± 0.03) |
| HA 2 mg/ml; Py 0.2M | (4.7 ± 0.4) * 10$^{-3}$ |
| HA 4 mg/ml; Py 0.2M | (2.9 ± 0.1) * 10$^{-3}$ |
| HAOSO$_3$ 0.9 mg/ml; Py 0.2M | (0.9 ± 0.1) |
| HAOSO$_3$ 0.33 mg/ml; Py 0.2M | (3.44 ± 0.05) |

Lastly, it was possible to compare the electric conductibility values with those reported in the literature for similar polymers (Synthesis and characterisation of polypyrrole-hyaluronic acid composite biomaterials for tissue engineering applications", Collier et al., J. Biomed. Mater. Res., 50, 574-584, 2000 (*—see Table 5); "Sulphonated polyurethane aniomer-polypyrrole molecular composite", G. Robila, M. Ivanoiu, T. & C. Buruiana, Journal of applied polymer science, 66, 591-595, 1997 (*—see Table 5); "Growth of polypyrrole at surface of sulphonated polyethylene", Rueda, Arribas, Calleja et al., Synthetic Metals, 28, C77-C81, 1989 (—see Table 5)):

TABLE 5

| Polypyrrole/Counterion Coupling | Conductibility [S/cm] |
|---|---|
| PPy/HA* | (3±) * 10$^{-3}$ |
| PPy/PE sulphonate** | 1–10 |
| PPy/PUA sulphonate*** | ~4.5 * 10$^{-6}$ |

The symbols reported in the table refer to the articles listed above.

EXAMPLE 5

Synthesis of Conductive Films Based On PPy/HAOSO$_3$ and HA On Gauzes of HYAFF®11p75 and 100

It was interesting to study the effect of the polymerisation of these conductive films on gauzes based on esterified HA. The first synthesis was conducted on gauzes of HYAFF®11p75, after studying their swelling kinetics in an aqueous solution. This experiment was conducted by immersing the woven material in a solution of HAOSO$_3^-$ (3.3 mg/ml) and of Py 0.1 M, to enable the exact experimental conditions to be reproduced for the synthesis. Some minutes later, the gauze had swollen to the maximum extent and lost its original consistency. This led the researchers to conduct a synthesis using the HYAFF®11p75 woven material exclusively as a means of dispersing the starting electrolytic solution. Swelling (S) was calculated as the ratio between the weight of the sample after immersion in the solution (W1) and the weight of the dry sample (W0):

$$S = \frac{W_1}{W_0}$$

as shown in FIG. 2.

Synthesis was conducted using the galvanostatic method and placing the gauzes soaked in the starting electrolytic solution between two glass electrodes, the surfaces of which are coated with a conductive film (ITO). Hereafter we report the various working conditions used to synthesise conductive films based on polypyrrole on HYAFF® woven materials.

TABLE 6

| POLYMER deposited on HYAFF ® | METHOD |
|---|---|
| PSS 0.1 M, Py 0.1M | Galvanostatic Total charge → 5.5 C |
| HAOSO$_3$ 3.3 mg/ml, Py 0.2M | Galvanostatic Total charge → 10.9 C |

These procedures were repeated using gauzes (woven and non-woven) with a greater degree of esterification (total HYAFF®11), in order to obtain conductive polymer films supported on HYAFF® that are more stable in aqueous solution than the previously illustrated cases.

Table 7 summarises the methods used in the synthesis.

TABLE 7

| POLYMER deposited on non-woven HYAFF ® | Current in the cell |
|---|---|
| HAOSO$_3$ 3.3 mg/ml, 0.2 M Py | 11.7 C |
| HAOSO$_3$ 3.3 mg/ml, 0.2 M Py | 6.72 C |
| POLYMER deposited on woven HYAFF ® | Current in the cell |
| HAOSO$_3$ 3.3 mg/ml, 0.2 M Py | 11.4 C |
| HAOSO$_3$ 0.9 mg/ml, 0.2 M Py | 8.58 C |
| HA 2 mg/ml, 0.2 M Py | 7.62 C |

EXAMPLE 6

Synthesis of Conductive Films Based on PPy/HAOSO$_3$ On Total HYAFF®11 Gauzes In Guide Channels To conduct this type of synthesis we used a cell constituted by a cylindrical working electrode in steel and a counter-electrode constituted by a copper mesh wrapped round the working electrode. The working electrode was inserted into the HYAFF® guide channel and immersed in the electrolytic solution, as was the counter-electrode. Hereafter we report the conditions used in the procedure.

Guide Channels of Total HYAFF®11, HAOSO$_3$ 3.3 mg/ml, Py 0.2M→Total Charge: ~14 C In this case it was not possible to calculate the electric conductibility of the samples directly, but it is possible to do so indirectly on the basis of the calculations of the conductibility of films of total HYAFF®11 (woven).

EXAMPLE 7

Synthesis of Conductive Films Based on PPy/HAOSO$_3$ on Gauzes of HYAFF® With a High Degree of Esterification.

The synthesis of conductive films based on polypyrrole was repeated using woven HYAFF® with a greater degree of esterification, in order to obtain a material that was more stable in aqueous solution while possessing different mechanical properties from the gauzes characterised previously.

The conditions employed in the synthesis are reported hereafter:

Polymer Films in HYAFF®, HAOSO$_3$ 3.3 mg/ml, Py 0.2M, 7.66 C.

As these super-esterified polymer films have a somewhat compact, not very rough surface, they could be used directly as supports for conductive films. It will be relatively easy to arrive at the absolute value of the electric conductibility of these new materials, contrary to our earlier experience with the electric conductor samples on gauzes of HYAFF® (11p75 and total 11—woven and non-woven).

This type of synthesis was conducted by the galvanostatic method using films of esterified HA with a thickness varying between 20-150 μm and applying a current of between 0.5 and 10 mA in the cell. The solutions of Py and electrolyte used reproduce those illustrated in the previous examples (concentration of pyrrole between 0.5 and 3M, concentration of polysaccharide in the form of a sodium salt varying between 0.9 and 5 mg/ml).

EXAMPLE 8

Estimate of the Electric Conductivity on Synthesised Polymer Films on Gauzes of HYAFF® at Different Degrees of Esterification.

We were able to estimate the electric conductibility of conductive polymer films based on polypyrrole supported on HYAFF® matrices with different degrees of esterification, by calculating their thickness indirectly according to the previously illustrated method.

Table 8 reports some of the more interesting results obtained.

TABLE 8

| Polymer deposited on woven gauzes of total HYAFF ® 11 | Charge [C] | Thickness [C] | R[Ω] | σ[S/cm] |
|---|---|---|---|---|
| HAOSO$_3$ 3.3 mg/ml, Py 0.2M | 6.84 | 9.25 * 10$^{-4}$ | (777 ± 4) * 10$^2$ | (3.07 ± 0.02) * 10$^{-3}$ |
| Polymer deposited on nonwoven gauzes of total HYAFF ® 11 | Charge [C] | Thickness [cm] | R[Ω] | σ[S/cm] |
| HAOSO$_3$ 3.3 mg/ml, Py 0.2M | 11.7 | 1.35 * 10$^{-3}$ | (301 ± 2) * 10$^2$ | (5.41 ± 0.04) * 10$^{-3}$ |
| HAOSO$_3$ 3.3 mg/ml, Py 0.2M | 6.72 | 1.24 * 10$^{-3}$ | (394 ± 2) * 10$^1$ | (4.51 ± 0.02) * 10$^{-2}$ |

The conductivity values thus obtained will be underestimated because the indirectly calculated thickness does not allow for penetration of the polymer film swelling within the meshes.

EXAMPLE 9

Variation In the Superficial Morphology of Conductive Polymer Samples Based on PPy Applied to the Electrode and on the Surfaces of Woven HYAFF®

SEM superficial morphological analysis was performed on synthesised samples (films deposited on glass electrodes and on woven HYAFF®), revealing a marked difference in growth mechanisms between the polymers based on PPy/PSS and the polymer films based on PPy/HA & HAOSO$_3$. Indeed, the polymers did not prove to grow homogeneously or at a constant rate because of the increase in the resistance on the working electrode and consequent alteration of the electric field inside the electrochemical cell.

The tests performed on the films showed, as reported in the literature ("Synthesis and characterisation of polypyrrole-hyaluronic acid composite biomaterials for tissue engineering applications", Collier et al., J. Biomed. Mater. Res., 50, 574-584, 2000), the presence of spherical aggregates distributed randomly on the surface ("Growth of polypyrrole at the surface of sulphonated polyethylene", Rueda, Arribas, Fierro et al., Synthetic Metals, 28, 1989, C77-C81).

The different morphology of the polymer films depends on many factors (synthesis charge density, nature and concentration of the solutions, nature of the conductive substrate) that play a crucial role in the beginning and termination of growth.

Since the synthesis mechanism occurs in a succession of steps (oxidation of the monomer, dimerisation, growth and oxidation with insertion of counterions), it is the slow stage of the process that determines the overall structure of the polymer. The morphological differences encountered are therefore linked, the other factors being equal, with the nature of the doping agents that are incorporated in the polypyrrole during electrochemical synthesis. It is therefore possible to note that in the case of PSS there is greater affinity with the polypyrrole chains and the PPy/PSS polymer shows a uniform, smooth structure. Conversely, HA and sulphated HA, in which the cyclo-alkyl chain can interact only marginally with the polypyrrole, exploiting its functional polar groups, show films with more porous, globular structures.

EXAMPLE 10

Synthesis of Polymer Films Based on PPy, HA and the Derivatives Thereof on Titanium Supports With a view to a possible application in the biomedical field, we synthesised films based on polypyrrole and biocompatible, macromolecular counterions (PSS, HA, HYOX, $HAOSO_3$ and the further derivatives thereof) deposited on titanium (alloys of Ti, Au and similar, biocompatible materials). Said materials present mechanical properties that are the total opposite of those of the conductive films deposited on HYAFF® and this may suggest their possible application in the orthopaedic field and in bone tissue regeneration.

Synthesis was conducted mainly in galvanostatic conditions using current ranges of 0.5-15 mA and concentrations of pyrrole varying between 0.05 and 0.3M. As in the previously described cases, we used concentrations of counterions varying between 0.9 and 5 mg/ml.

The entire metal mesh at the end of the process proves to be completely coated with a thin layer of electroconductive material. These synthesis processes are conducted on sheets and tubes in titanium, previously coated with HYAFF® with a high degree of esterification, in order to obtain a material as biocompatible and structurally resistant as possible.

EXAMPLE 11

Scheme of a Cell for Serial Electrochemical Synthesis for Application on a Medium Scale.

The syntheses described till now can be conducted using a cell for serial electrochemical synthesis. In this way, the time it takes to synthesise the single samples can be notably reduced.

Said cell is constituted by several reaction chambers wherein the electrodes are connected together serially. By using the galvanostatic method in each reaction cell a continuous stream of current with constant intensity will be obtained, so the only limiting factor for the sequential number of cells used will be the drop in electrical potential that will occur at the end of each single couple of electrodes once synthesis has begun.

This type of cell is reported in the annexed FIG. 3, wherein is shown a generic circuit with serial electrochemical cells.

The invention claimed is:

1. A composite biomaterial constituted by:
    (a) an electrically conductive polymer film based on polypyirole (PPy) and at least one compound chosen from the group formed by hyaluronic acid, ester derivatives of hyaluronic acid (HYAFF), O-sulphated derivatives of hyaluronic acid ($HAOSO_3$), or percarboxylated derivatives of hyaluronic acid (HYOXX) and,
    (B) a two- or three-dimensional structure constituted by at least one ester derivatives of hyaluronic acid (HYAFF), percarboxylated derivatives of hyaluronic acid (HYOXX), autocrosslinked derivatives of hyaluronic acid (ACP), or crosslinked derivatives of partially deacetylated hyaluronic acid.

2. A composite biomaterial according to claim 1, wherein the ester derivative of hyaluronic acid (HYAFF) is a 75% partial ester or a total ester.

3. A composite biomaterial according to claim 1, wherein the O-sulphated derivative of hyaluronic acid ($HAOSO_3$) has a degree of sulphation of between 2 and 4.

4. A composite biomaterial according to claim 1, wherein the percarboxylated derivative of hyaluronic acid (HYOXX) has a degree of oxidation of between 50 and 100%.

5. A composite biomaterial according to claim 3 or 4, wherein $HAOSO_3$ and HYOXX serve as doping agents and nerve regenerators.

6. A composite biomaterial according to claim 1, wherein polypyrrole (PPy) is the electroconductor and doping agent.

7. A composite biomaterial according to claim 1, wherein the two- or three-dimensional structure is constituted by a woven fabric, non-woven felt, membrane, film, gauze, meshed net, guide channel, or sponge.

8. A composite biomaterial according to claim 1, wherein the two- or three-dimensional structure is constituted by an ester derivative of hyaluronic acid (HYAFF) that is a 75% partial ester or a total ester.

9. A composite biomaterial according to claim 1, wherein the two- or three-dimensional structure is constituted by a percarboxylated derivative of hyaluronic acid (HYOXX) with a degree of oxidation of between 50 and 100%.

10. A composite biomaterial according to claim 1, wherein the two- or three-dimensional structure is constituted by an autocrosslinked derivative of hyaluronic acid (ACP) with a degree of crosslinking of between 1 and 100%.

11. A composite biomaterial according to claim 1, wherein the two- or three-dimensional structure is constituted by a partially deacetylated crosslinked derivative of hyaluronic acid.

12. A process for the preparation of a composite biomaterial according to claim 1 comprising the following steps:
    (a) purification of the pyrrole and
    (b) electrochemical polmerization of the pyrrole in the presence of an electrolyte, supported by a two- or three-dimensional polysaccharide matrix based on hyaluronic acid derivatives.

13. A process according to claim 12, where the pyrrole is purified by filtration through alumina or distillation in a vacuum.

14. A process according to claim 12, where the electrochemical polymerization is performed either potentiostatically or galvanostatically.

15. A process according to claim 12, wherein polystyrene sulphate (PSS), hyaluronic acid and the derivatives thereof constituted by hyaluronic acid with various degrees of sulphation, or percarboxylated HA (HYOXX) are used as electrolytes during the step of polymerization of the pyrrole.

16. A process according to claim 12, wherein the supporting polymer matrix may be constituted by membranes, woven fabrics and non-woven felts based on hyaluronic acid derivatives belonging to the ester groups (HYAFF), autocrosslinked derivatives (ACP), derivatives crosslinked from partially de-N-deacylated hyaluronic acid, or percarboxylated derivatives (HYOXX).

17. A composite biomaterial according to claim 1, wherein the O-sulphated derivative of hyaluronic acid (HA-$OSO_3$) has a degree of sulphation of between 2.5 and 3.5.

18. A method of using a composite biomaterial according to claim 1 for the regeneration of nerve and bone tissue.

19. A method of using a composite biomaterial according to claim 1 for the growth and differentiation of nerve cells and in the repair of damaged nerves with consequent recovery of lost nervous function.

20. A composite biomaterial consisting of polypyrrole and biocompatible, macromolecular counterions selected from PSS, HA, HYOXX, HA$OSO_3$ and derivatives thereof deposited on titanium or titanium alloys for use in the orthopaedic field and in bone tissue regeneration.

* * * * *